United States Patent [19]
Guo et al.

[11] Patent Number: 5,378,033
[45] Date of Patent: Jan. 3, 1995

[54] MULTI-FUNCTION MECHANICAL HAND WITH SHAPE ADAPTATION

[75] Inventors: Gongliang Guo, Lexington, Ky.; Xikang Qian, Beijing, China; William A. Gruver, British Columbia, Canada

[73] Assignee: University of Kentucky Research Foundation, Lexington, Ky.

[21] Appl. No.: 60,104

[22] Filed: May 10, 1993

[51] Int. Cl.⁶ ............................................. B25J 15/10
[52] U.S. Cl. .................................. 294/116; 294/115; 623/64; 901/38; 901/39
[58] Field of Search ................ 294/106, 111, 115, 116; 623/57, 64; 901/36–39

[56] References Cited

U.S. PATENT DOCUMENTS

| | | | |
|---|---|---|---|
| 1,507,682 | 9/1924 | Pecorella et al. | 623/64 X |
| 2,553,827 | 5/1951 | Mason | 623/64 |
| 2,869,139 | 1/1959 | Mosher | 294/106 X |
| 3,345,647 | 10/1967 | Gentiluomo | 901/38 X |
| 3,694,021 | 9/1972 | Mullen | 294/106 |
| 3,866,966 | 2/1975 | Skinner | 294/106 |
| 3,901,547 | 8/1975 | Skinner | 294/115 X |
| 3,927,424 | 12/1975 | Itoh | 294/106 X |
| 4,094,016 | 6/1978 | Eroyan | 901/38 X |
| 4,142,426 | 3/1979 | Baranyi et al. | |
| 4,225,983 | 10/1980 | Radocy et al. | |
| 4,258,441 | 3/1981 | Bell | |
| 4,291,421 | 9/1981 | Massey et al. | |
| 4,315,650 | 2/1982 | Yoshida | 901/36 X |
| 4,351,553 | 9/1982 | Rovetta et al. | 294/106 |
| 4,364,593 | 12/1982 | Maeda | 294/106 |
| 4,650,492 | 3/1987 | Barkhordar et al. | 901/39 X |
| 4,792,338 | 12/1988 | Rennerfelt | 623/64 |
| 4,834,443 | 5/1989 | Crowder et al. | 294/106 |
| 4,946,380 | 8/1990 | Lee | 294/111 X |
| 4,980,626 | 12/1990 | Hess et al. | 901/37 X |
| 5,062,673 | 11/1991 | Mimura | 294/111 |

OTHER PUBLICATIONS

Guo et al, "Design of A Planar Multijointed Prosthetic Finger Mechanism" (Date unknown) pp. 165–170.

Caporali, et al "Design and Construction of a Five-Fingered Robotic Hand", *Robotics Age*, Feb. 1984, pp. 14–20.

Bekey et al, "Control Architecture for the Belgrade/USC Hand", *Dextrous Robot Hands*, 1990, pp. 137–149.

Rakic', Miodrag "Multifingered Robot Hand with Selfadaptability" *Robotics & Computer Integrated Manufacturing* vol. 5, No. 2/3 pp. 269–276, 1989.

Peizer, Edward "Research trends in upper limb prosthetics" *Atlas of Limb Prosthetics: Surgical and Prosthetic Principles* pp. 219–258, 1981.

Kato, Ichiro, *Mechanical Hands Illustrated*, 1987, pp. 3–34.

Jacobsen et al, "The UTAH/MIT Dextrous Hand: Work in Progress", *The International Journal of Robotics Research*, vol. 3 No. 4, Winter 1984, pp. 21–49.

Cutkosky, Mark R. "On Grasp Choice, Grasp Models, and the Design of Hands for Manufacturing Tasks" *IEEE Transactions on Robotics and Automation*, vol. 5 No. 3 Jun. 1989 pp. 269–279.

*Primary Examiner*—Johnny D. Cherry
*Attorney, Agent, or Firm*—King & Schickli

[57] ABSTRACT

A mechanical hand assembly for use in prosthetic and robotic applications includes multiple fingers pivotally attached to a palm subassembly. The fingers are operatively attached to a central actuating plate so that movement of the actuating plate in opposed directions causes the fingers to bend and straighten. An electric motor drives the actuating plate through a pivotable or tiltable linkage so that when one of the fingers engages an object to be manipulated, the plate tilts and continues to move any opposed fingers toward engagement. Each finger includes a base, a lever arm and multiple phalanges operatively interconnected by gears. Pivotal motion of the lever arm is transmitted to the phalanges through the interconnected phalanges and lever arm and rotation of the gears. The palm subassembly also includes a finger-spacing plate that fixes the relative positions of the fingers, and a finger orientation plate that, when rotated, changes the orientations of the fingers and the planes through which they bend. This makes it possible to selectively converge the tips of only two of the fingers, three of the fingers or to bend all of the fingers in an interdigitating manner.

20 Claims, 6 Drawing Sheets

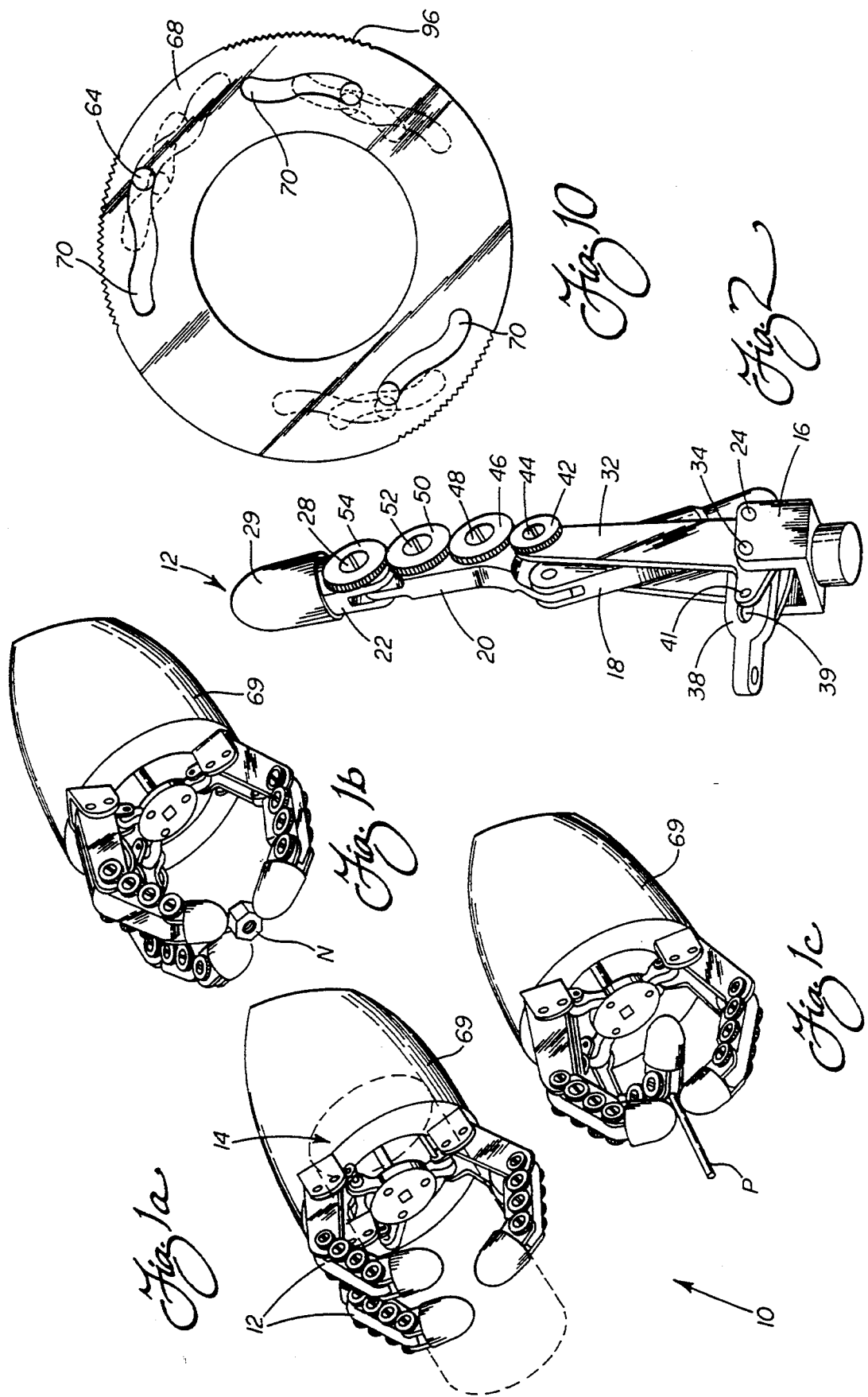

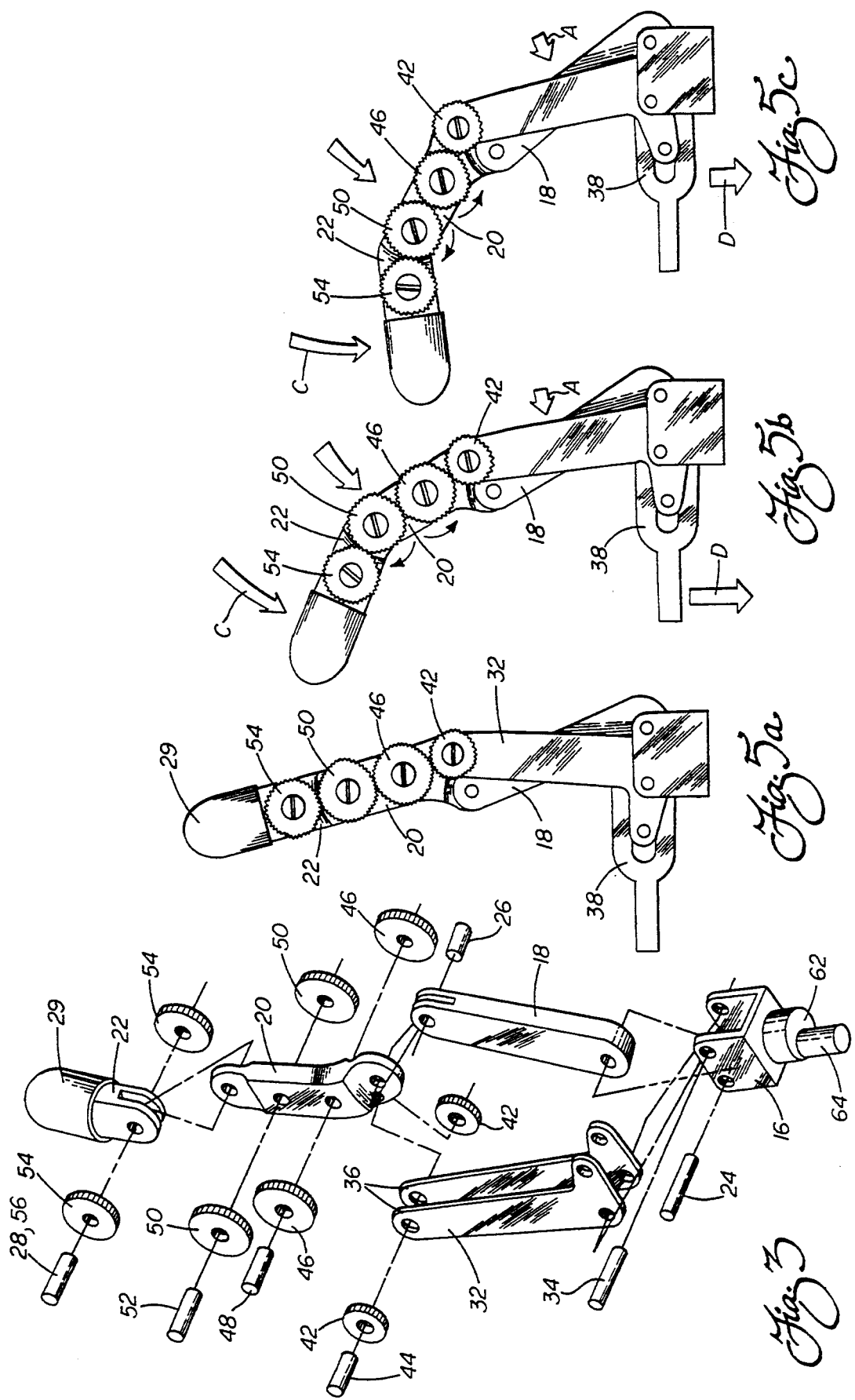

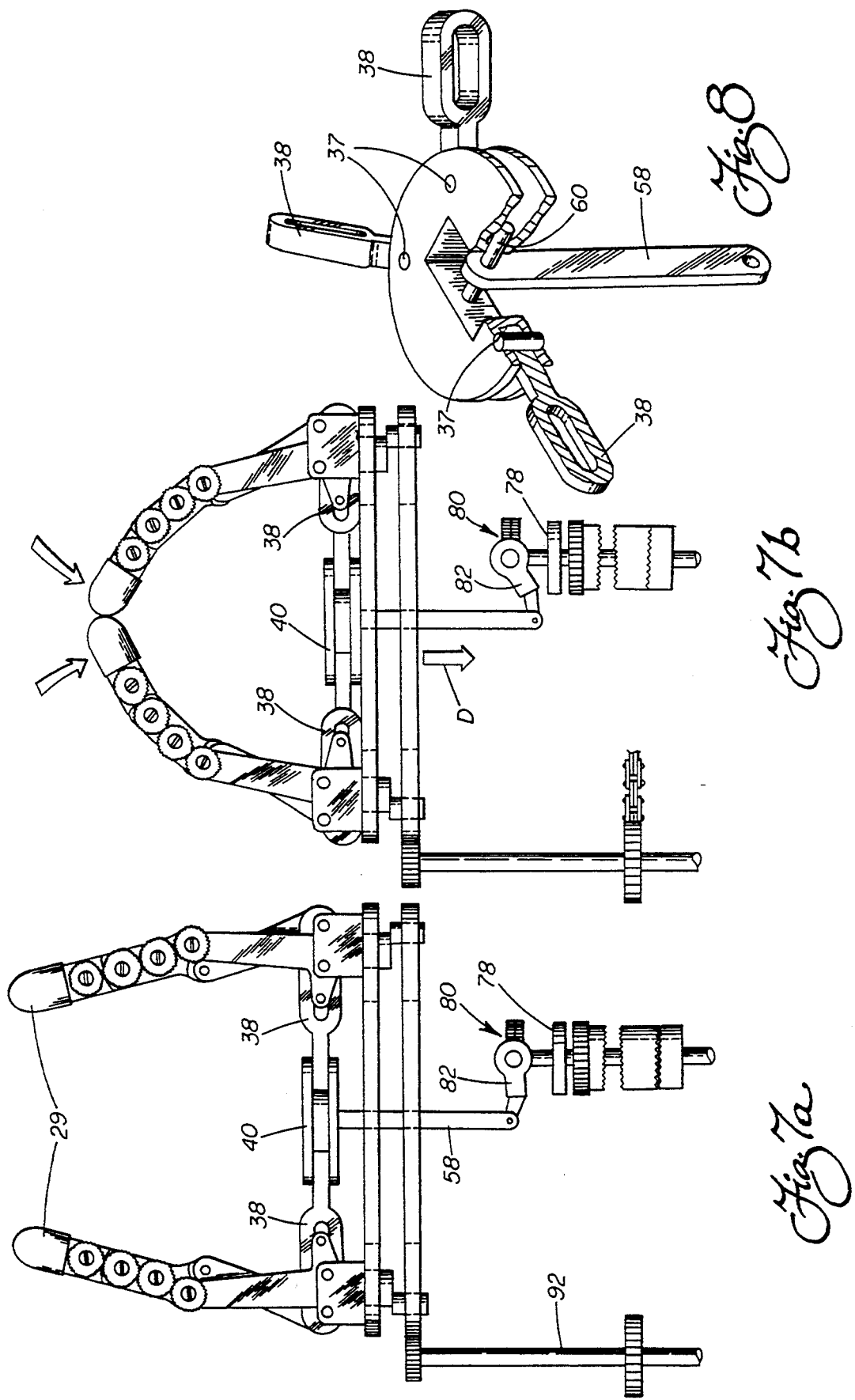

MULTI-FUNCTION MECHANICAL HAND WITH SHAPE ADAPTATION

TECHNICAL FIELD

The present invention relates to a mechanical hand assembly for use in prosthetic and robotic applications, and more particularly, to an improved assembly whereby a single drive means bends/straightens all the fingers and further provides for shape adaptation and for adjusting the orientation of the individual fingers to perform multiple functions.

BACKGROUND OF THE INVENTION

Many different types and forms of artificial or mechanical hands are known, providing a variety of functions and uses. A mechanical hand assembly as discussed herein is, however, distinguishable from a purely cosmetic artificial hand because it is functional, i.e. can be used to grip an object or perform some other task performed by a human hand.

One significant use of mechanical hand assemblies is in prosthetics wherein they replace the form and function of human hands that have been amputated or otherwise lost. Mechanical hands give amputees the ability to perform tasks, such as writing or handling articles, requiring dexterous manipulation of an object.

Another important use of mechanical hand assemblies is in cooperation with industrial robotics. Automatically controlled mechanical hand assemblies replace expensive manual labor and are, at the same time, more repetitive, exact and error-free than the manual counterpart. This results in increased productivity for two reasons. First, fewer laborers are required to produce the same quantity and, second, human errors are reduced so the quality is improved. Mechanical hand assemblies are also used in hazardous industrial environments precluding the use of human hands. Mechanical hand assemblies may also be used to perform certain tasks in areas with tight space constraints. This is particularly true where these areas are otherwise inaccessible to a human hand.

As a result of the vast number of beneficial applications for mechanical hand assemblies, many designs have evolved. In general, they include multiple fingers separated into phalanges and attached to a base or palm subassembly. Functional mechanical hand assemblies, i.e. those that are not merely a cosmetic or prosthetic replacement, include means for bending and straightening the fingers to simulate movement of the human hand.

An important feature of the human hand and particularly the fingers is the ability to bend around an object and adapt to its shape. Specifically, bending of a finger is controlled so that the finger stops upon engaging the object. In contrast, the other fingers continue to bend until they too engage the object. The significant number of prior mechanical hand assemblies include several that have means for shape adaptation. Specifically, the 1989 article by Rakic, entitled "Multi-fingered Robot Hand With Self-adaptability", *Robotics & Computer-Integrated Manufacturing*, Vol. 5, No. 2/3, pp. 269-276 discloses a mechanical hand assembly that uses a lever between adjacent fingers. The lever allows adjacent fingers to bend unevenly to conform to a curved surface (FIG. 1 and page 271 column 2). This shape adaptation is, however, available only between adjacent, non-opposed fingers that bend toward the object in substantially the same direction.

Another type of prior art mechanical hand assembly uses numerous proximity sensors mounted on phalanges of the fingers to detect when the fingers engage an object. A complex computer control system receives signals from the sensors and interrupts the bending of the phalanges on engagement with the object. An example of such a mechanical hand assembly is disclosed in Hess et al. U.S. Pat. No. 4,980,626 to Hess et al.

In yet another approach, the torque of the motors that bend the fingers is monitored. Rising torque is indicative of engagement of a finger with an object. Thus, upon sensing rising torque, power to the motor driving that finger is interrupted. Just such an approach is utilized in, for example, U.S. Pat. No. 5,062,673 to Mimura.

Despite all of these advances in shape adaptation, a relatively full function mechanical hand has still yet to be developed. More specifically, it must further be appreciated that imitating the bending of human fingers to perform different tasks is difficult because human fingers bend individually to perform some tasks and in different, selected planes relative to one another to perform others. For example, holding a pencil between two fingers requires much different finger bending than holding a ball. A mechanical hand assembly capable of different functions must provide means to change the cooperative bending relationships, that is, the bending planes of the individual fingers.

Some prior art mechanical hand assemblies include multiple motors/drive means to actuate bending of the fingers. They allow the fingers to bend independently so that, by actuating some of the motors and not actuating others, different cooperative bending relationships are achieved. An example of a mechanical hand assembly incorporating multiple drive motors is U.S. Pat. No. 5,080,682 to Schectman wherein individual motors drive each of the five fingers (see FIG. 1). A problem with such an approach is, of course, their relatively complicated structure that is more expensive to produce and less reliable in operation than desired simply because of the sheer number of component parts.

Another problem in imitating the bending of human fingers is the movement of the outermost phalanges during bending. A human finger includes three phalanges, the outermost of which exhibits the greatest range of movement during bending. To simulate this in a mechanical hand assembly requires an operative interconnecting means between the outermost phalange and either the palm subassembly, wherein the actuating means is located, or another phalange that is operatively interconnected to the palm subassembly.

Various methods for effecting movement of the outermost phalange are disclosed in prior art mechanical hand assemblies. For example, the Schectman '682 patent discloses a complicated cable and pulley arrangement wherein pulleys mounted on the phalanges of the fingers are attached by cables to the palm subassembly. Such an approach is unfortunately, cumbersome and relatively bulky. It is also expensive to design, produce and maintain over time.

It should further be appreciated that all prior mechanical hand assemblies known to these inventors are significantly limited in that the orientation of the fingers is fixed due to secure mounting to the palm subassembly. This results in the fingers always bending in the same direction or plane. As discussed above, some assemblies include shape adaptation means including multiple drive motors and mechanical linkages providing for differential bending of the fingers after they contact the object, but none modify the orientation of the fingers on the palm subassembly to effect different cooperative bending relationships between the fingers and thereby allow the performance of different functions such as pinching, grasping and holding.

A mechanical hand assembly that can perform multiple functions is more versatile and efficient, replacing several assemblies that can each perform a single function. For example, a mechanical hand assembly that can effectively pinch a small object between two fingers or hold a large object between all the fingers is valuable because two separate mechanical hand assemblies are not necessary.

Summarizing, prior art mechanical hand assemblies provide functional replacements that substantially simulate the motion of a human hand and are thus useful. However, these prior art assemblies have many disadvantages. First, the multiple drive means necessary for shape adaptation require a complicated mechanical assembly and a very complex control system. This complexity makes them expensive to design and manufacture. They are also difficult and expensive to maintain, troubleshoot, and repair because of the complexity and because so many fallible components are included. Multiple drive motors, complicated cable/pulley or linkage connections in the fingers, touch sensors mounted on the phalanges, and complicated computer control systems provide a great number of potential sources of malfunction.

Prior art mechanical hand assemblies are also limited in their capabilities. For instance, in those including provisions for shape adaptation, only those fingers bending toward an object from substantially the same direction adapt to the shape of the object. That is, none teach a mechanical hand assembly wherein the bending of opposing fingers, i.e. those on opposite sides of an object bending toward the object in substantially opposite directions, is adaptable. Prior art mechanical hand assemblies are further limited because the secure mounting of the fingers to the palm subassembly fixes the orientation of the fingers. None provide for reorientation to effectively provide different cooperative bending relationships between the fingers as are necessary to perform different functions.

A particular need is, therefore, identified for an improved mechanical hand assembly with a simple construction and provisions for shape adaptation and multiple function operation. Specifically, means for bending the fingers utilizing a single drive means and allowing opposing fingers to adapt to the shape of an object being manipulated is needed. In addition, the need for a mechanical hand assembly capable of orientation adjustment of the fingers and an improved means for effecting movement of the outermost phalange simulating that of a human finger is desired.

SUMMARY OF THE INVENTION

Accordingly, it is a primary object of the present invention to provide a mechanical hand assembly for gripping an object in prosthetic and robotic applications overcoming the above described limitations and disadvantages of the prior art.

Another object of the invention is to provide a mechanical hand assembly wherein all the fingers are mechanically connected together such that a single drive means causes all the fingers to bend and straighten.

It is yet another object of the present invention to provide a mechanical hand assembly wherein the finger linkage allows opposing fingers to adapt to the shape of an object. This is accomplished through a pivoting central plate linked to all the fingers.

It is another object to provide a mechanical hand assembly equipped with means for changing the orientations of the fingers to cause them to selectively adopt different cooperative bending relationships. Specifically, the orientation of the plane of bending of each of the fingers may be selectively adjusted so that the fingers are capable of performing multiple functions. Thus, the fingers are advantageously capable of bending so that they may "pinch" an object between two finger tips, "grasp" an object between three finger tips, or "hold" an object by bending in parallel in an interdigitating manner.

A further object is to provide a clutch as part of the mechanical hand assembly so that the same drive means for actuating bending/straightening of the fingers also drives the mechanism allowing the orientation adjustment necessary for multiple function capability. In this way the overall design is simplified while also providing unprecedented versatility and overall performance.

Another object of the invention is to provide a mechanical hand assembly wherein a cooperating linkage and intermeshing gears mounted on the phalanges of the fingers provide the means for effecting movement of the outermost phalanges simulating that of a human finger.

Additional objects, advantages and other novel features of the invention will be set forth in part in the description that follows and in part will become apparent to those skilled in the art upon examination of the following or may be learned with the practice of the invention. The objects and advantages of the invention may be realized and obtained by means of the instrumentalities and combinations particularly pointed out in the appended claims.

To achieve the foregoing and other objects, an improved mechanical hand assembly is provided wherein an actuating means effects bending/straightening of all the fingers. A means for selectively driving the actuating means in a first/second direction causes bending/straightening. The mechanical hand assembly advantageously eliminates the need for drive means for each finger or each phalange, thereby also eliminating the need for numerous mechanical linkages or a complex control system relating to the drives. Accordingly, the present mechanical hand assembly is a simpler construction and less costly to design, manufacture, and maintain than prior art assemblies.

The mechanical hand assembly also includes means for shape-adapting the bending of the fingers to conform to an object being handled. Specifically, a central plate is provided mechanically linking all the fingers. This central plate is linked to the drive by a pivot connection. This allows the central plate to tilt so that, if the bending of one finger is stopped due to engaging the object, bending of the remaining, opposed fingers continues. In this way the fingers adapt to the shape of an object with equal pressure applied by each. Advantageously, this design makes shape adaptation possible without the provision of complex and expensive sensors or control systems, as are found in prior art mechanical hand assemblies.

The mechanical hand assembly of the present invention also includes an improved means for operatively interconnecting the phalanges in each finger to move the outermost phalange in a range of motion similar to a human finger. Intermeshing gears mounted on the phalanges of each finger transmit the pivotal motion of an associated lever arm, that is secured to the palm subassembly, to the second and third phalanges. These intermeshing gears eliminate the more complicated, more expensive and less reliable cable/pulley and linkage arrangements commonly found in the prior art.

Means for adjusting the orientations of the fingers to effect different cooperative bending relationships is also provided so that the mechanical hand assembly can perform multiple functions. In one relationship, the tips of exactly two of the fingers converge to pinch an object between them. In a second relationship, the tips of three of the fingers converge to grasp an object located between them. In a third relationship, the fingers bend in parallel in an interdigitating manner with opposing fingers closing together so that an object is held between them. This capability makes this mechanical hand assembly more versatile than its prior art counterparts and, therefore, suited for more and varied applications. Advantageously, it should also be appreciated that this mechanical hand assembly utilizes a single drive means to power the actuating means for bending/straightening the fingers and the orientation adjustment means. Thus, a most efficient and economical overall design is achieved.

Still other objects of the present invention will become apparent to those skilled in this art from the following description wherein there is shown and described a preferred embodiment of the invention, simply by way of illustration of one of the modes best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

FIGS. 1a-1c schematically illustrate the mechanical hand assembly functioning, respectively, to hold, grasp and pinch an object as a result of different, selected, coordinated bending relationships of the fingers;

FIG. 2 is a detailed perspective view of a finger separate from the rest of the mechanical hand assembly;

FIG. 3 is an exploded view of a finger showing the phalanges, lever arm, base, and tip and the pivotal pin connections and gears between them;

FIGS. 5a-5c schematically illustrate in detail the bending of each finger and relative rotations of the gears mounted thereon during bending;

FIGS. 7a and 7b illustrate the bending of the fingers and the relationship to the motion of the central plate and the driving linkage;

FIG. 8 is a detailed sectional view of the central plate illustrating the pivotal connection between it and the drive linkage allowing tilting for shape adaptation;

FIG. 10 is a detailed view of the grooved annular plate illustrating the three positions of the eccentric cams resulting in the three orientations of the finger bases and three cooperative bending relationships of the fingers shown in FIGS. 1a-1c.

DETAILED DESCRIPTION OF THE INVENTION

Figure 4:
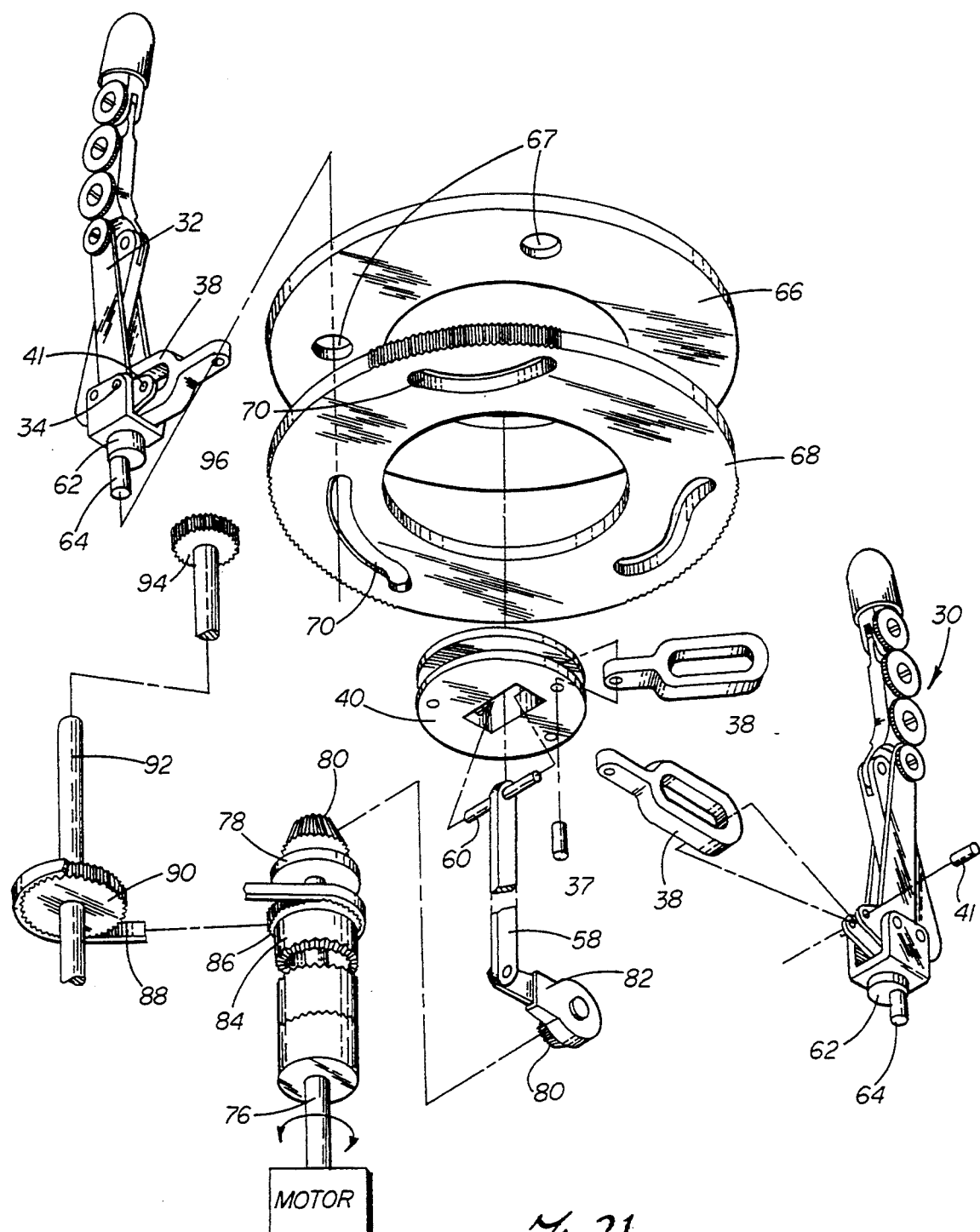
FIG. 4 is a partially exploded bottom perspective view of the mechanical hand specifically illustrating the relationship between the finger-spacing plate, the grooved annular plate and the finger bases, and a central plate and means for linking all of the fingers thereto.

Reference is now made to FIGS. 1a-1c showing a mechanical hand assembly 10 including three fingers 12 mounted to a palm subassembly generally shown at reference numeral 14. As is known in the art, the fingers 12 are made to bend and straighten to simulate the movement of human fingers. In this way, the mechanical hand assembly 10 can be used as a replacement for the human hand in both prosthetic and robotic applications.

As shown in more detail in FIGS. 2 and 3, each finger 12 includes a base or yolk 16 and three interconnected, cooperating phalanges 18, 20, 22. The first phalange 18 is pivotally mounted at a proximal end to the base 16 by pivot pin 24. The proximal end of the second phalange 20 is pivotally mounted to the distal end of the first phalange 18 by means of pivot pin 26. Finally, the proximal end of the third phalange 22 is pivotally mounted to the distal end of the second phalange 20 by pivot pin 28. A resilient "finger tip" 29 of a type known in the art caps the distal end of the third phalange 22.

Bending/straightening of the fingers 12 is provided by means of a combined linkage and gear arrangement, generally designated by reference numeral 30. Specifically, each finger 12 includes a lever arm 32 that is pivotally mounted by means of a pin 34 to the base 16. As shown, the lever arm 32 is split so as to include a pair of spaced uprights 36 defining a gap therebetween sufficiently wide to allow free passage of the first phalange 18. The proximal end of each lever arm 32 is connected by means of a transfer link 38 (see FIG. 2) and cooperating pin 37 to a central plate actuator 40 of the palm subassembly 14, the operation of which will be described in greater detail below. Specifically, the transfer link 38 includes an elongated opening 39 to accommodate the arcuate movement of the connecting pin 41 during pivoting of the lever arm 32.

The distal end of the lever arm 32 includes a pair of stationary gears 42 fixed in place by fasteners 44. The gears 42 mesh with a second set of gears 46 mounted on the second phalange 20 for relative rotary movement by means of stub shafts 48. The gears 46 mesh in turn with a third set of gears 50 mounted on the second phalange for relative rotary movement by means of stub shafts 52. The gears 50 mesh, in turn, with a fourth set of gears 54 that are fixed in place on third phalange 22 by means of fasteners 56.

In operation, movement of the central plate actuator 40 is transmitted through the transfer links 38 to the lever arms 32. The lever arms 32 pivoting about pins 34 effect rotation of second phalanges 20, connected to the lever arms 32 by pins 44 and to first phalanges 18 by pins 26. During the pivoting and rotation, the first set of stationary gears 42 drives the second set of rotary gears 46. Additionally, the second set of gears 46 drives the third set of rotary gears 50 which in turn mesh with the fourth set of stationary gears 54. As a result, the third phalange 22 is pivoted about pin 28 relative to the second phalange 20.

Ratios between the gears 42, 46, 50, 54 are selected and established so that the pivotal motion of the third or outermost phalange 22 is the largest (note action arrow C in FIGS. 5b and 5c) and the pivotal motion of the first or base phalange 18 is the smallest (note action A). This allows full bending of the fingers 12 until they converge as in FIGS. 7a and 7b, with very small movements of the central actuating plate 40. For instance, the fingers 12 converge as shown in FIG. 7b from a fully open position in response to only approximately 5 mm of travel by the central plate actuator 40 in the direction indicated by action arrow D. Thus, it should be appreciated that the fingers 12 may be selectively folded or bent together when the central plate actuator 40 is driven in a first direction and selectively straightened when the central plate actuator is driven in a second opposite direction. Further, bending and straightening occurs in a smooth responsive manner substantially mimicking actual movement of the fingers of the human hand.

Figure 6C:
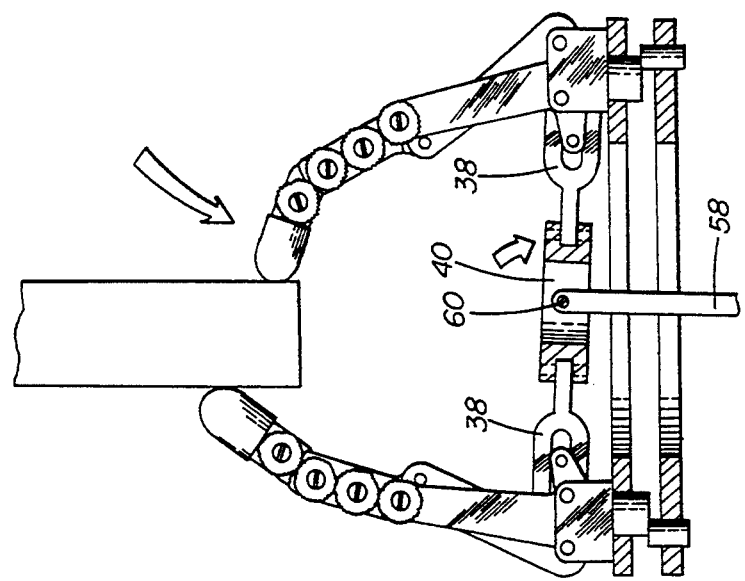
FIGS. 6a-6c illustrate the shape adaptation of opposing fingers of the present hand assembly with specific illustration of the tilting of the central plate in FIG. 6c.
Figure 6B:
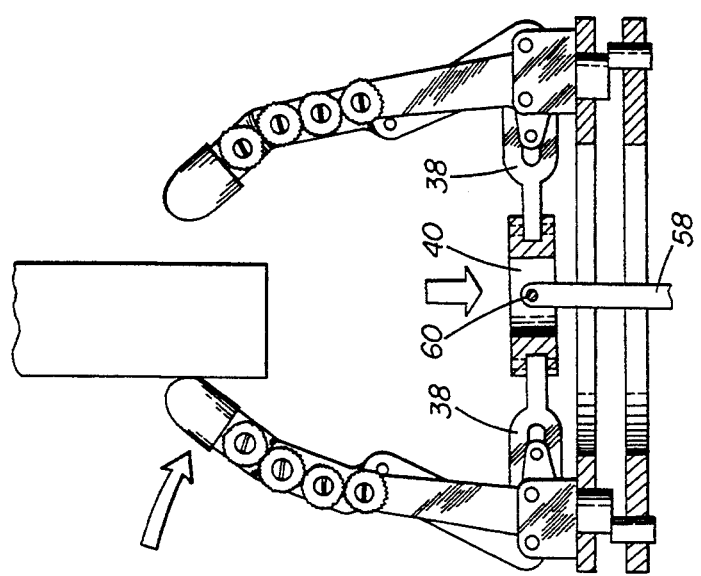
Figure 6A:
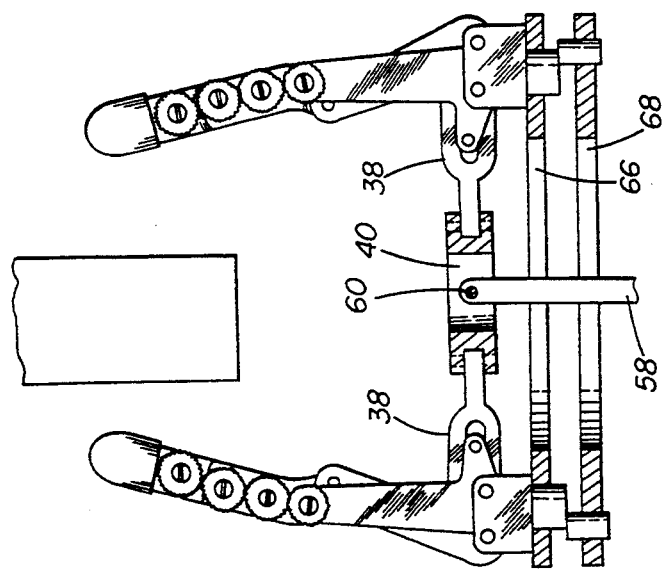

The adaptability of the fingers 12 to conform to the shape of an object being handled is best shown with reference to FIGS. 6a-6c. Specifically, this shape adaptability is provided through the pivotal connection of the central plate actuator 40 to the drive arm 58. As shown, the central plate actuator 40 is mounted to the drive arm 58 by means of the dual pivot pin 60. This pivotal connection makes it possible for movement of the central plate actuator 40 and other, opposing fingers 12 to continue even after the first finger has contacted the object.

With specific reference to FIGS. 6a and 6c, the central plate actuator 40 initially remains perpendicular to the drive arm 58, closing all the fingers 12 in unison. This is because the resistance to the closing of all the fingers 12 is initially equal. However, once one of the fingers 12 engages the object (see FIG. 6b), resistance to the further closing of that finger increases and this causes the central plate actuator 40 to tilt (see FIG. 6c) about the dual pivot pin 60. As the plate 40 tilts, the other, opposing finger(s) continues to close until it contacts the object equalizing the resistance to closing between the opposing fingers. Thus, through this mechanism the fingers 12 are bent so that opposing finger tips 29 apply equal pressure when an object is irregularly shaped and/or grasped by the hand assembly 10 when in an off-center position. The pivotal connection of the dual pin 60, shown in more detail in FIG. 8, allows a maximum tilt of approximately 10° as indicated in FIG. 6c.

The orientation of the fingers 12, e.g. the orientation of the planes of finger bending, is also selectively adjustable in the present design. To achieve this end, the base 16 of each finger 12 includes a cylindrical mounting stem 62 that carries an eccentric cam 64. Additionally, the palm subassembly 14 includes an annular, finger spacing plate 66 having an annular opening for the passage of the central plate actuator 40 and spaced apertures 67 for receiving the cylindrical stems 62 of the fingers 12. The apertures 67, therefore, set the spacing of the fingers 12 but also allow relative rotary movement between the stems 62 and the spacing plate 66. Thus, the orientation of the plane of bending of the individual fingers 12 may be adjusted.

The palm subassembly 14 also includes an annular, finger orientation plate 68 that also has an annular opening for the passage of the central plate actuator 40. The plates 66 and 68 are mounted with proper spacing maintained therebetween by the outer housing 69 that supports the hand assembly 10 (see FIGS. 1a-1c). The orientation plate 68 includes a series of spaced, irregularly shaped grooves 70, each groove receiving an eccentric cam 64 of one of the fingers 12 (see also FIG. 10). Accordingly, the eccentric cams 64 of the fingers 12 ride in the grooves 70. As a result, rotation of the orientation plate 68 relative to the finger spacing plate 66 causes, by operation of the eccentric cam 64, the fingers 12 to rotate on their stems 62 in the plate 66. Thus, the finger bending planes are effectively adjustable so as, for example, to allow holding, grasping and pinching functions as shown, respectively, in FIGS. 1a-1c.

More specifically, when oriented for holding, the planes of finger bending are all substantially parallel so as to provide for interdigitating, bending action of the fingers 12 (see FIG. 1a). In contrast, when oriented for grasping, the planes of finger bending are oriented to intersect at a central, intermediate position above the central actuator plate 40 between the fingers 12. Thus, grasping of a small object, such as nut N is possible (see FIG. 1b). Finally, when oriented for pinching, the planes of finger bending for two opposing fingers 12 are identically aligned to allow pinching of an object such as a pin P (see FIG. 1c). The plane of bending for the remaining finger or fingers is oriented in a different plane so as not to interfere with the pinching action.

Advantageously, the mechanisms described for (1) finger bending/straightening, (b) shape adaptability, and (c) finger orientation are all driven by means of a single motor 72 through a drive linkage and transmission generally designated by reference numeral 74.

Figure 9:
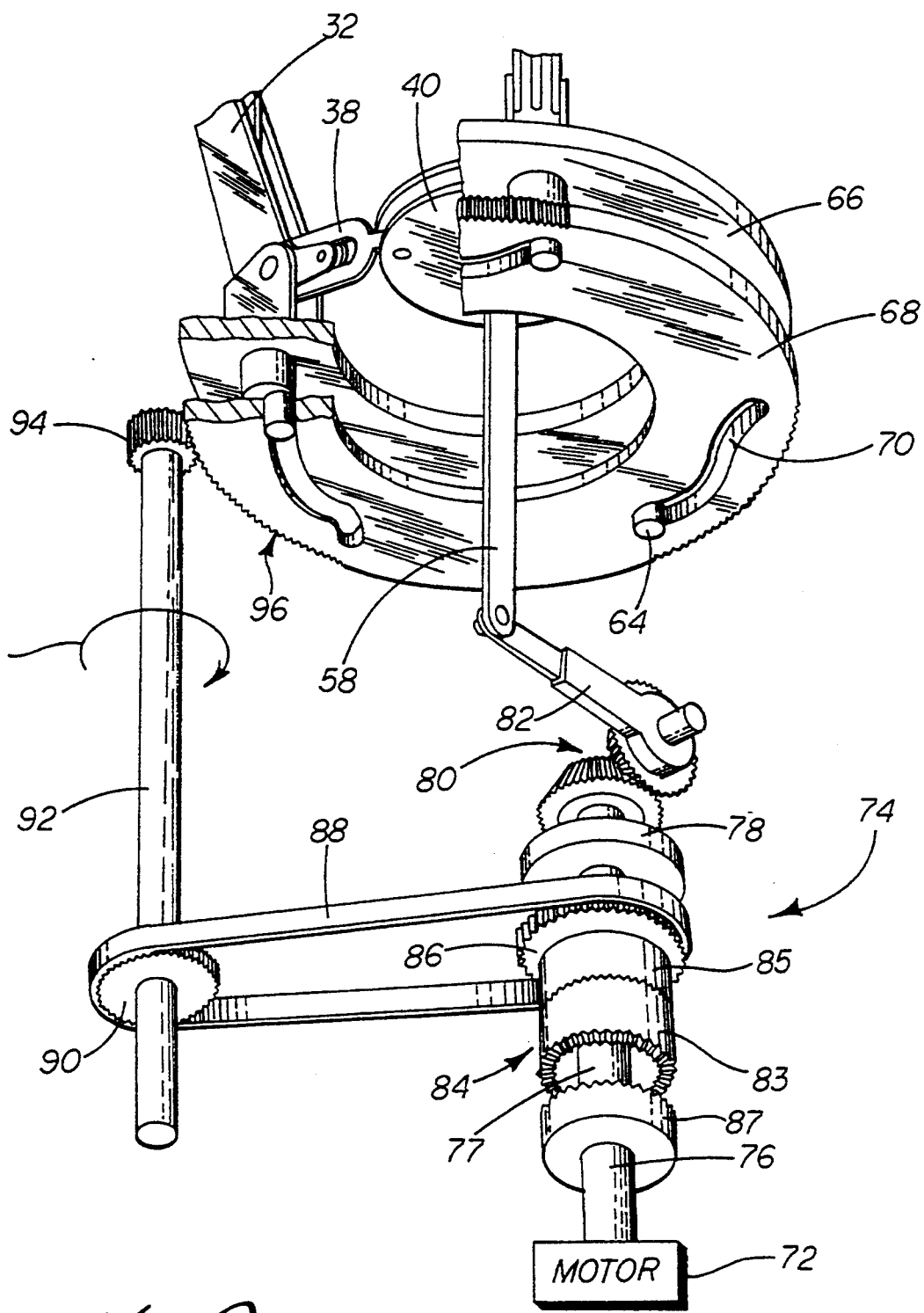
FIG. 9 is a partially sectional bottom perspective view of the palm subassembly illustrating the drive motor to bend/straighten the fingers and the clutch selectively coupling the drive motor to rotate the finger orientation plate and provide selective finger orientation.

Finger bending/straightening is provided by operating the motor 72 in forward and reverse directions, respectively. More specifically with reference to FIG. 9, the motor 72 drives output shaft 76. The output shaft 76 is selectively connected through a two-position clutch 84 of, for example, the electromagnetic type, to an input shaft 77 extending from the lower clutch drive wheel 87 to the transmission 78. The output shaft 76 extends through lower clutch drive wheel 87 and is positively attached to clutch fly wheel 83. Rotary motion of the shaft 76 is transmitted through cooperation of a transmission 78, bevel gear pair 80, a rotary arm 82 and the drive arm 58 to provide linear up and down movement of the dual pivot pin 60 about which the central plate actuator 40 is pivotally mounted. This movement is next transmitted through the transfer links 38, lever arm 32 and gear sets 42, 46, 50, 54 to bend/straighten the fingers 12. Of course, as already described above, any shape adaptability required to grasp the object being handled is automatically provided between opposing fingers 12 by the pivotal movement of the central plate actuator 40 on the end of the drive arm 58.

Selective finger orientation is also provided by operating the motor 72 in forward and reverse directions. More specifically, the motor 72 drives the output shaft 76. The clutch is operated so that the clutch fly wheel 83 engages the upper clutch drive wheel 85. Thus, the output shaft 76 is selectively connected through the clutch 84 to a gear 86, belt 88, gear 90, driven shaft 92 and gear 94 to transmit power to the annular finger orientation plate 68. More particularly, the teeth on gear 94 mesh with teeth 96 provided along the outer edge of the plate 68. Thus, the rotational motion of the gear 94 causes rotation of the finger orientation plate 68 relative to the finger spacing plate 66. As described above, this causes the eccentric cams 64 to ride along the grooves 70 rotating the finger mounting stems 62 in the spacing apertures 67 of the plate 66. In this way, the plane of bending of the fingers 12 is adjusted to allow for the separate functions of holding, grasping and pinching.

In summary, an improved mechanical hand assembly 10 is provided wherein a single drive means 72 actuates bending and straightening of all the fingers 12 to simulate a human hand. In addition, means for shape-adaptation is provided so that the fingers 12 bend so as to apply equal pressure to the object. The mechanical hand assembly 10 also includes provisions for performing multiple functions by adjusting the orientations of the fingers and the directions in which they bend. Three different cooperative bending relationships allow the mechanical hand assembly to perform three functions; "holding", "grasping" or "pinching" an object. A significant benefit is the use of the same drive means for bending/straightening and adjusting the orientation of the fingers.

This single drive arrangement advantageously eliminates the need for multiple drives to bend/straighten fingers. It also eliminates the complicated cable/pulley or linkage arrangements disclosed in the prior art, replacing them with intermeshing gears 42, 46, 50, 54 mounted on the phalanges 18, 20, 22 that provide exceedingly reliable operation over a long service life. Its simple shape adaptation means eliminates the complicated and relatively expensive sensor/computer control assemblies of the prior art. Finally, its provisions for adjusting the orientations of the finger bases 16 allow the mechanical hand assembly 10 to perform multiple functions without requiring a redesign of the entire assembly. Hence, the overall versatility of the design is outstanding.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as is suited to the particular use contemplated. All such modifications and variations are within the scope of the invention as determined by the appended claims when interpreted in accordance with breadth to which they are fairly, legally and equitably entitled.

We claim:

1. A mechanical hand assembly for gripping an object in prosthetic and robotics applications comprising:
a plurality of fingers, each finger including a base, a plurality of pivotally interconnected phalanges and means for bending/straightening said plurality of fingers to simulate human finger movement;
an annular palm subassembly including means for engaging each said finger base and holding said fingers in relative, spaced operative positions substantially around a periphery of said annular palm subassembly and means, moveable relative to said engaging means, for actuating said finger bending/straightening means in concert, movement of said actuating means in a first direction bending all of said fingers and movement of said actuating means in a second direction straightening all of said fingers; and
means for selectively driving said actuating means in said first and second directions.

2. A mechanical hand assembly as set forth in claim 1 wherein said actuating means includes a central plate operatively linked to all said finger bending/straightening means.

3. A mechanical hand assembly as set forth in claim 2 further including means for shape-adapting the bending of said fingers to conform to the object being gripped.

4. A mechanical hand assembly as set forth in claim 3 wherein said shape-adapting means includes a pivotal linkage between said driving means and said central plate allowing tilting of said central plate whereby when one of said fingers engages said object, said central plate tilts allowing further movement of said central plate and closing on said object of all remaining, opposed fingers.

5. A mechanical hand assembly as set forth in claim 1 wherein each finger base includes a cylindrical stem and said finger base engaging means includes a finger spacing plate with apertures fitted to receive for relative rotary movement said cylindrical stem from each of said finger bases thereby allowing rotation of said finger bases.

6. A mechanical hand assembly as set forth in claim 5 wherein each of said fingers includes an outermost tip and said assembly further includes means for rotating said finger bases in said finger-spacing plate whereby orientations of the planes through which the fingers bend may be adjusted to selectively effect three cooperative bending relationships: in a first of said relationships said outermost tips of exactly two of said fingers converge; in a second said outermost tips of three of said fingers converge; and in a third all said fingers bend along parallel planes in an interdigitating manner.

7. A mechanical hand assembly as set forth in claim 6 wherein said finger base rotating means includes:
an annular finger orientation plate including irregularly shaped grooves therein;
an eccentric cam extending from each said finger base stem, the positions of said cams defining the orientation of said finger bases as determined by said cams engaging and riding in said irregularly shaped grooves;
means for rotating said finger orientation plate whereby the positions of said cams are changed, rotating said finger bases and adjusting the orientations of the planes through which the fingers bend.

8. A mechanical hand assembly as set forth in claim 7 wherein said finger orientation plate rotating means includes:
a drive shaft;
gear teeth on an outer edge of said finger orientation plate;
gear means on said drive shaft for engaging said teeth on said edge of said finger orientation plate whereby said finger orientation plate is rotated; and clutch means for releasably coupling said selective driving means to said finger orientation plate drive shaft.

9. A mechanical hand assembly as set forth in claim 8 wherein:
said driving means includes a reversible electric motor and a clutch assembly coupled to an output shaft of said electric motor.

10. A mechanical hand assembly as set forth in claim 1 wherein said bending/straightening means includes:
a lever arm pivotally connected to each finger base;
means for operatively interconnecting said lever arm and said phalanges including intermeshing gears mounted on said lever arm and said phalanges;
means for pivoting said lever arm whereby relative pivoting of said phalanges and bending of said fingers is provided in a manner so as to simulate human finger movement.

11. A mechanical hand assembly as set forth in claim 10 wherein each of said fingers includes a first phalange pivotally connected at a proximal end to said base, a second phalange pivotally connected at a proximal end to a distal end of said first phalange, and a third phalange pivotally connected at a proximal end to a distal end of said second phalange and wherein said intermeshing gears include one non-rotary gear mounted on said lever arm, two rotary gears mounted in series on said second phalange, and one non-rotary gear mounted on said third phalange.

12. A mechanical hand assembly as set forth in claim 11 wherein ratios are selected between said intermeshing gears to cause said pivoting of said third phalange to be greater than said pivoting of said second phalange, and said pivoting of said second phalange to be greater than said pivoting of said first phalange during said bending/straightening of said finger.

13. A mechanical hand assembly for gripping an object in prosthetic and robotic applications comprising:
a plurality of fingers, each finger including a base, a lever arm and first phalange both pivotally connected to said base, a second phalange pivotally connected to a distal end of said first phalange and a third phalange pivotally connected to a distal end of said second phalange;
each of said bases further including a cylindrical stem and an eccentric cam extending from said stem;
a palm subassembly including both a finger-spacing plate with apertures fitted to receive said cylindrical stems and a finger orientation plate with irregularly shaped grooves receiving said eccentric cams;
a central plate mechanically linked to all of said fingers, movement of said central plate in a first direction actuating bending of all of said fingers together, movement in a second direction actuating straightening of all of said fingers;
an electric motor driving said central plate in said first and second directions;
intermeshing gears for operatively interconnecting said lever arm and said first, second and third phalanges including a non-rotary gear mounted on said lever arm, two rotary gears mounted in series on said second phalange and a non-rotary gear mounted on said third phalange;
a drive shaft imparting rotary motion to said finger orientation plate; and
clutch means for releasably coupling said electric motor to said finger orientation plate drive shaft.

14. The mechanical hand assembly as set forth in claim 13, further including means for shape-adapting the bending of said fingers to conform to the object being handled.

15. A mechanical hand assembly as set forth in claim 14 wherein said shape-adapting means includes a pivotal linkage connecting said drive means and said central plate whereby when one of said fingers engages said object, said central plate tilts allowing further movement of said central plate and closing of all remaining, opposed fingers.

16. A mechanical hand assembly for gripping an object in prosthetic and robotics applications comprising:
a plurality of fingers, each finger including a base having a cylindrical stem, a plurality of pivotally interconnected phalanges and means for bending/straightening said plurality of fingers to simulate human finger movement;
a palm subassembly including means for engaging each said finger base and holding said fingers in relative, spaced operative positions and means for actuating said finger bending/straightening means, movement of said actuating means in a first direction bending all of said fingers and movement of said actuating means in a second direction straightening all of said fingers;
means for selectively driving said actuating means in said first and second directions;
said finger base engaging means including a finger spacing plate with apertures fitted to receive for relative rotary movement said cylindrical stem from each of said finger bases thereby allowing rotation of said finger bases; and
means for rotating said finger bases in said finger-spacing plate including an annular finger orientation plate having irregularly shaped grooves therein, an eccentric cam extending from each said finger base stem, the positions of said cams defining the orientation of said finger bases as determined by said cams engaging and riding in said irregularly shaped grooves, and means for rotating said finger orientation plate whereby the positions of said cams are changed, rotating said finger bases and adjusting the orientations of the planes through which the fingers bend.

17. A mechanical hand assembly as set forth in claim 16 wherein said finger orientation plate rotating means includes:
a drive shaft;
gear teeth on an outer edge of said finger orientation plate;
gear means on said drive shaft for engaging said teeth on said edge of said finger orientation plate whereby said finger orientation plate is rotated; and
clutch means for releasably coupling said selective driving means to said finger orientation plate drive shaft.

18. A mechanical hand assembly as set forth in claim 17 wherein:
said driving means includes a reversible electric motor and a clutch assembly coupled to an output shaft of said electric motor.

19. A mechanical hand assembly for gripping an object in prosthetic and robotics applications comprising:
a plurality of fingers, each finger including a base;
a first phalange pivotally connected at a proximal end to said base, a second phalange pivotally connected at a proximal end to a distal end of said first phalange, and a third phalange pivotally connected at a proximal end to a distal end of said second phalange;

a palm subassembly including means for engaging each said finger base and holding said fingers in relative, spaced operative positions and means for actuating said finger bending/straightening means, movement of said actuating means in a first direction bending all of said fingers and movement of said actuating means in a second direction straightening all of said fingers;

means for selectively driving said actuating means in said first and second directions;

said bending/straightening means including a lever arm pivotally connected to each finger base, means for operatively interconnecting said lever arm and said phalanges including intermeshing gears mounted on said lever arm and said phalanges;

said intermeshing gears including one non-rotary gear mounted on said lever arm, two rotary gears mounted in series on said second phalange, and one non-rotary gear mounted on said third phalange; and means for pivoting said lever arm whereby relative pivoting of said phalanges and bending of said fingers is provided in a manner so as to simulate human finger movement.

20. A mechanical hand assembly as set forth in claim 19 wherein ratios are selected between said intermeshing gears to cause said pivoting of said third phalange to be greater than said pivoting of said second phalange, and said pivoting of said second phalange to be greater than said pivoting of said first phalange during said bending/straightening of said finger.

* * * * *